United States Patent [19]

Matsuoka et al.

[11] 4,105,020

[45] Aug. 8, 1978

[54] BLOOD PRESSURE AND PULSE RATE MEASURING APPARATUS

[75] Inventors: Yoshifumi Matsuoka, Yamatotakada; Takemasa Matsumura, Toyonaka; Koichi Shigematsu, Kawanishi; Atsushi Oishi, Yaizu, all of Japan

[73] Assignee: Matsushita Electric Industrial Co., Ltd., Osaka, Japan

[21] Appl. No.: 686,395

[22] Filed: May 14, 1976

[30] Foreign Application Priority Data

| May 16, 1975 | [JP] | Japan | 50-58815 |
| May 29, 1975 | [JP] | Japan | 50-73201[U] |
| May 29, 1975 | [JP] | Japan | 50-73202[U] |

[51] Int. Cl.² .............................................. A61B 5/02
[52] U.S. Cl. ........................... 128/2.05 A; 128/2.05 T
[58] Field of Search .................... 128/2.05 R, 2.05 P, 128/2.05 T, 2.05 A, 2.05 M, 2.06 F

[56] References Cited

U.S. PATENT DOCUMENTS

| 3,051,165 | 8/1962 | Kompelien | 128/2.05 A |
| 3,192,921 | 7/1965 | Erickson et al. | 128/2.05 R |
| 3,229,686 | 1/1966 | Edmark, Jr. | 128/2.05 R |
| 3,536,062 | 10/1970 | Horn | 128/2.05 R |
| 3,978,848 | 9/1976 | Yen et al. | 128/2.05 M |

OTHER PUBLICATIONS

Randall, M. J., *Proceedings of the I.E.E.E.*, vol. 63 No. 10, Oct. 1975, pp. 1399-1403.

Primary Examiner—Kyle L. Howell
Attorney, Agent, or Firm—Stevens, Davis, Miller & Mosher

[57] ABSTRACT

In conventional blood pressure measuring apparatus, the simultaneous measurement of a pulse rate and a blood pressure is difficult without the use of complicated attachment devices. In this invention, a pulse rate measuring circuit is provided along with a blood pressure measurement apparatus for a simultaneous measurement of both pulse rate and blood pressure. Both measurements are derived from at least one microphone signal contained in a cuff-device. The pulse rate measuring circuit is designed to commence counting of the number of pulses after at least two Korotkoff's sounds have been detected and continues counting until a predetermined number is reached while the time period required for counting the predetermined number of pulses is measured. The pulse rate is determined by dividing the predetermined number by the measured time period.

3 Claims, 5 Drawing Figures

BLOOD PRESSURE AND PULSE RATE MEASURING APPARATUS

This invention relates to a blood pressure measuring apparatus having an additional function of a pulse rate counting.

Conventional apparatus is known which can be used for both blood pressure measurement and pulse rate counting, but no apparatus has been commercially proposed for enabling the measurement of a pulse rate during the measurement of blood pressure, without use of any special attachment.

Blood pressure measuring apparatus, a pulse rate meter and other instruments have been employed for a medical examination of the human circulatory system. Usually a Riva-Rocci method is applied for the measurement of blood pressure wherein Korotkoff's sounds are detected by a microphone to determine systolic and diastolic blood pressures. On the other hand, the detection of a pulse at a finger tip and other parts of human body is applied to the pulse rate meter. When it is necessary to know the pulse rate as an aid in diagnosis in conjunction with a blood pressure measurement, the pulse rate is measured again by a pulse rate meter or by a doctor's manual examination after the measurement of blood pressure. If the blood pressure and pulse rate can be simultaneously measured without having duplicate measurements, it would be possible to make a more integrated judgement on the basis of information of the pulse rate in the diagnosis relying upon blood pressure measurement, and also it would save troublesome procedures. Therefore, a need exists for an instrument having the function of measuring both blood pressure and pulse rate. In addition, it is desirable to achieve this dual function by a simple technique in which a pulse rate measurement is added to blood pressure measurement apparatus without any increased complexity in the apparatus employed such as the addition of devices, particularly detection devices near a conventional arm band of the blood pressure measurement apparatus.

Furthermore, in an apparatus wherein the measurements of blood pressure and pulse rate are simultaneously and automatically conducted it is not until the conditions of both the determination of diastotic blood pressure and the termination of pulse rate measurement are simultaneously satisfied that the entire measurement is completed. When the above condition is not fulfilled, for example, the diastolic blood pressure has been determined before the measurement of pulse rate is finished or vice versa, and consequently if counting and other functions are stopped by the completion of either the determination of diastolic blood pressure or the measurement of pulse rate, the above measurements would not yield worthwhile information.

This invention is designed to overcome the above-mentioned disadvantages of conventional devices.

An object of this invention is to provide an apparatus wherein the counting of pulse rate is conducted together with the measurement of blood pressure. Another object of this invention is to achieve simultaneous detection of both the Korotkoff's sounds and the number of heart beats by means of a single microphone. A further object of this invention is to provide an apparatus wherein no signal representing the termination of measurement is generated until the conditions of both determination of diastolic blood pressure and termination of pulse rate measurement are fulfilled.

These and other objects and features of the present invention may best be understood by making reference to the following description, taken in conjunction with the accompanying drawings, in which.

According to the present invention, a blood pressure measuring apparatus having a cuff-device including at least one microphone is provided for detecting Korotkoff's sounds. The apparatus which enables simultaneous measurement of a blood pressure and a pulse rate comprises; a means for counting the number of pulses contained in a signal detected by the microphone, a means for initiating the counting of the counting means after at least two Korotkoff's sounds are ascertained, a means for measuring a time period required for the counted number of pulses to reach a predetermined number, and a means connected to the pulse counting means and the time period measuring means for calculating a pulse rate by dividing the predetermined number of pulses by the required time period.

Figure 1:
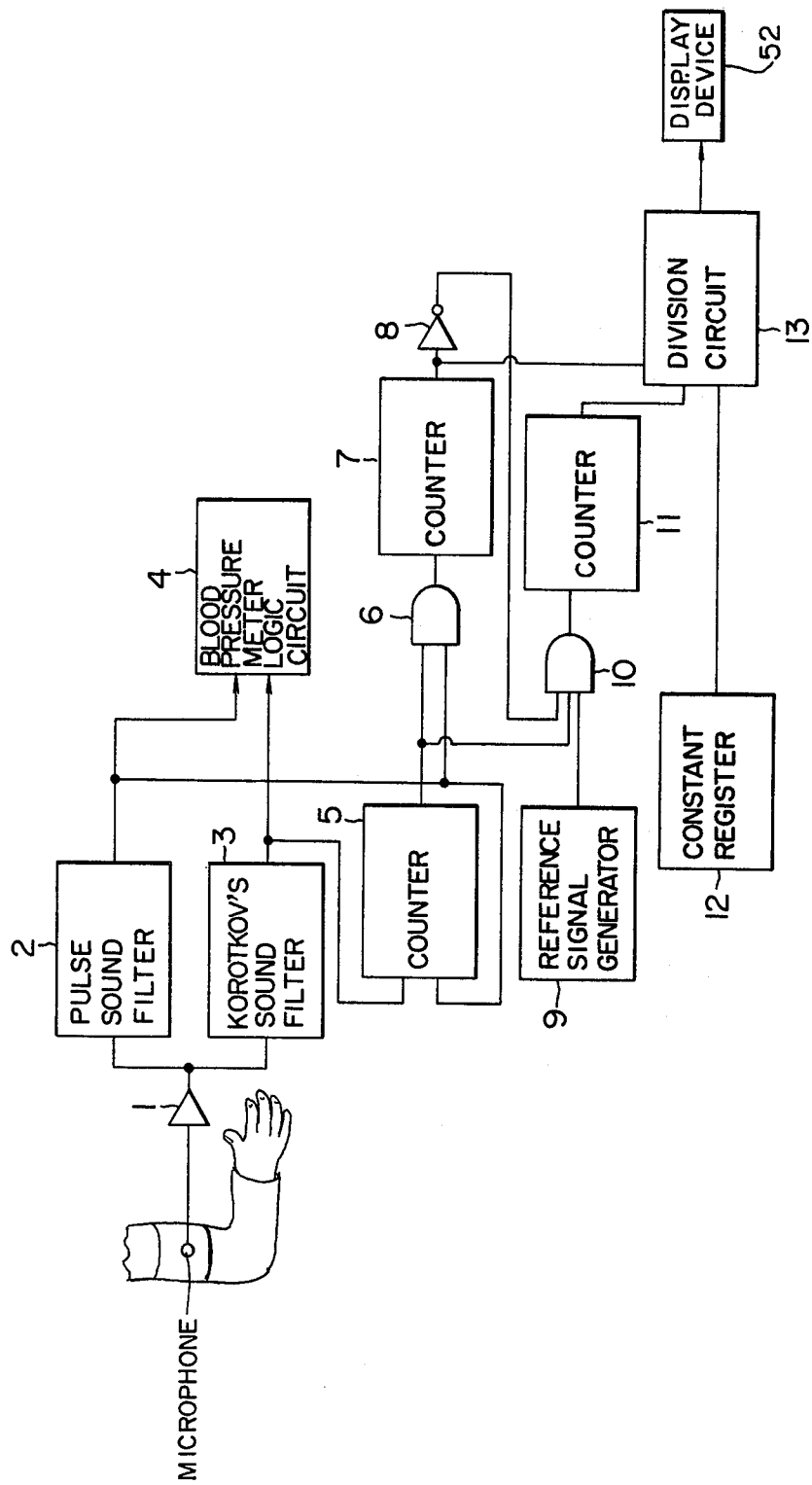
FIG. 1 is a block diagram of an embodiment of the invention.

An embodiment of this invention is shown in FIG. 1. Referring to the diagram, an output of a microphone 51 for detection of Korotkoff's sounds which is contained in a cuff-device 50 is amplified in an amplifier 1 and split into two signals; one signal passing through a filter 2 for detecting only pulse sounds and the other signal passing through a filter 3 for separating only the Korotkoff's sounds. The systolic and diastolic blood pressures are determined in a blood pressure meter logic circuit 4.

A pulse rate counting device used in the invention utilizes the pulse sound signal from the filter 2 and the Korotkoff's sound signal from the filter 3. A counter 5 has its output set at a high level for the first time after two Korotkoff's sound signals from the filter 3 are successively generated in synchronism with the pulse sound signal from the filter 2. Numeral 6 designates an AND circuit. After the counter 5 is set at the high level, the AND circuit 6 allows the pulse sound signal from the filter 2 to pass and actuates a counter 7. After counting a predetermined number K of pulse sounds, the counter 7 sets its output at a high level, and consequently sets an output of an inverter 8 at a low level, the inverter 8 being directly connected to the counter 7. Numeral 9 designates a reference signal generator. A counter 11 counts the reference signals after the output of the counter 5 is set at the high level until the counter 7 counts the predetermined number. In other words, the counter 11 measures a time period required for the number of pulses to reach the predetermined number K. For example, suppose that the counter 7 is set so that it counts 10 pulses and a 100 Hz oscillator is used as the reference signal generator. If an examinee having the pulse rate of 60 per minute is examined, the working time of the counter 7 is 10 seconds because the pulse rate is one per second. It follows that the counter 11 counts 100 × 10 = 1000 in 10 seconds. If the value of 60,000 is preset in a constant register 12, and if a division circuit 13 performs the division of 60,000 by an output of the counter 11, that is 1,000, the division circuit 13 yields 60. The division circuit 13 is arranged so that division is conducted when the counter 7 finishes counting K of the predetermined number of pulses.

Figure 2:
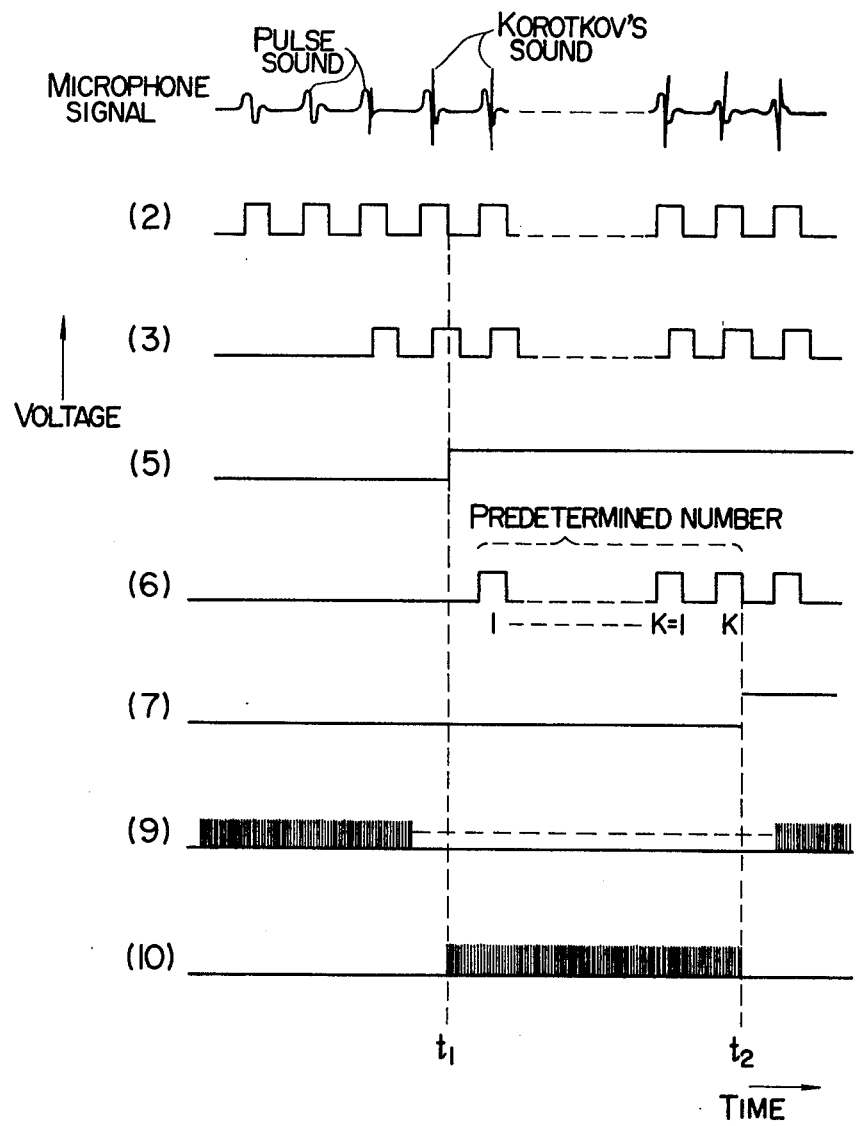
FIG. 2 shows waveforms of outputs obtained from various portions shown in corresponding blocks in FIG. 1.

The waveforms of output signals observed at several parts of the apparatus are shown in FIG. 2. The numbers at the left side of the diagrams indicate output waveforms observed at blocks in FIG. 1 having those numbers. The uppermost waveform in FIG. 2 is a signal from a microphone which contains both pulse sounds and Korotkoff's sounds. In the diagram the time between $t_1$ and $t_2$ indicates a pulse counting time. Reference signals which occur during this counting time are measured by the counter 11. FIGS. 1 and 2, illustrate that the Korotkoff's sounds are continuously generated during the counting of pulses up to the predetermined number of K. However, even if the Korotkoff's sounds disappear during course of the counting, this causes no problem if the counter 5 maintains its preset condition and the measurement of blood pressure continues until pulses are counted up to the predetermined number.

Alternatively, the number of pulses may be counted in the following way. After separating the Korotkoff's sound signal from the pulse sound signal by filters 2 and 3, the systolic and diastolic blood pressures are determined by the blood pressure meter logic circuit 4, and at same time the pulse sound signal alone is applied to the counter 7. In this counter 7, pulse sound signals are counted for a predetermined time period, or a time period in which a predetermined number of pulse signals occur is measured, whereby a calculation of the pulse rate can be made from the inverse of the measured time period. Then the counted pulse sound signals are converted into the number of pulses in one minute and the pulse rate obtained is displayed on a display device 52.

Figure 3:
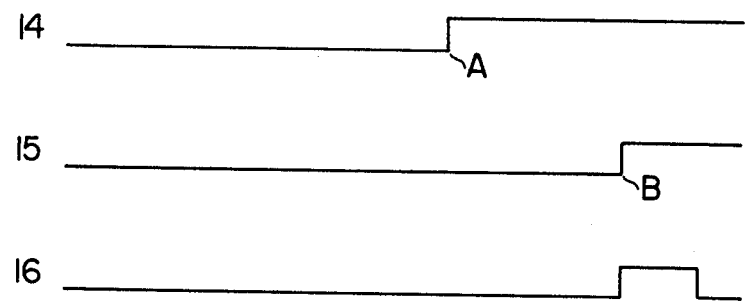
FIG. 3 shows signal waveforms which are useful to explain a manner of producing a measurement termination signal.
Figure 4:
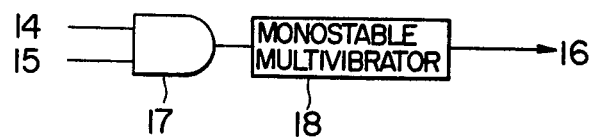
FIG. 4 shows a portion of circuitry for producing the measurement termination signal.

FIG. 3 and 4 illustrate how to generate a signal indicating the termination of measurement when the conditions of both the completion of the determination of the diastolic blood pressure and the termination of measurement of pulse rate are fulfilled. In the diagrams numeral 14 designates a diastolic blood pressure determination signal which is generated by the blood pressure meter logic circuit 4 as shown in FIG. 1, numeral 15 is a pulse rate measurement termination signal which is an output of the counter 7 as shown in FIG. 1, numeral 16 is a completion of measurement termination signal, numeral 17 is an AND circuit and numeral 18 is a monostable multivibrator.

These diagrams refer to the case where the diastolic blood pressure is determined before the termination of pulse rate measurement, in which case A and B respectively indicate the times of diastolic blood pressure determination and of termination of pulse rate measurement.

In operation, signals 14 and 15 which shift from low to high level at the diastolic blood pressure determination point A and pulse rate measurement termination point B respectively are generated, and in the AND circuit 17 logical product is produced from the signals 14 and 15. A monostable circuit 18 is driven by the logical product signal to generate the completion of measurement termination signal 16. This measurement termination signal 16 may be used to indicate to examiners the termination of both measurements by using adequate devices such as a buzzer and a flash lamp.

Figure 5:
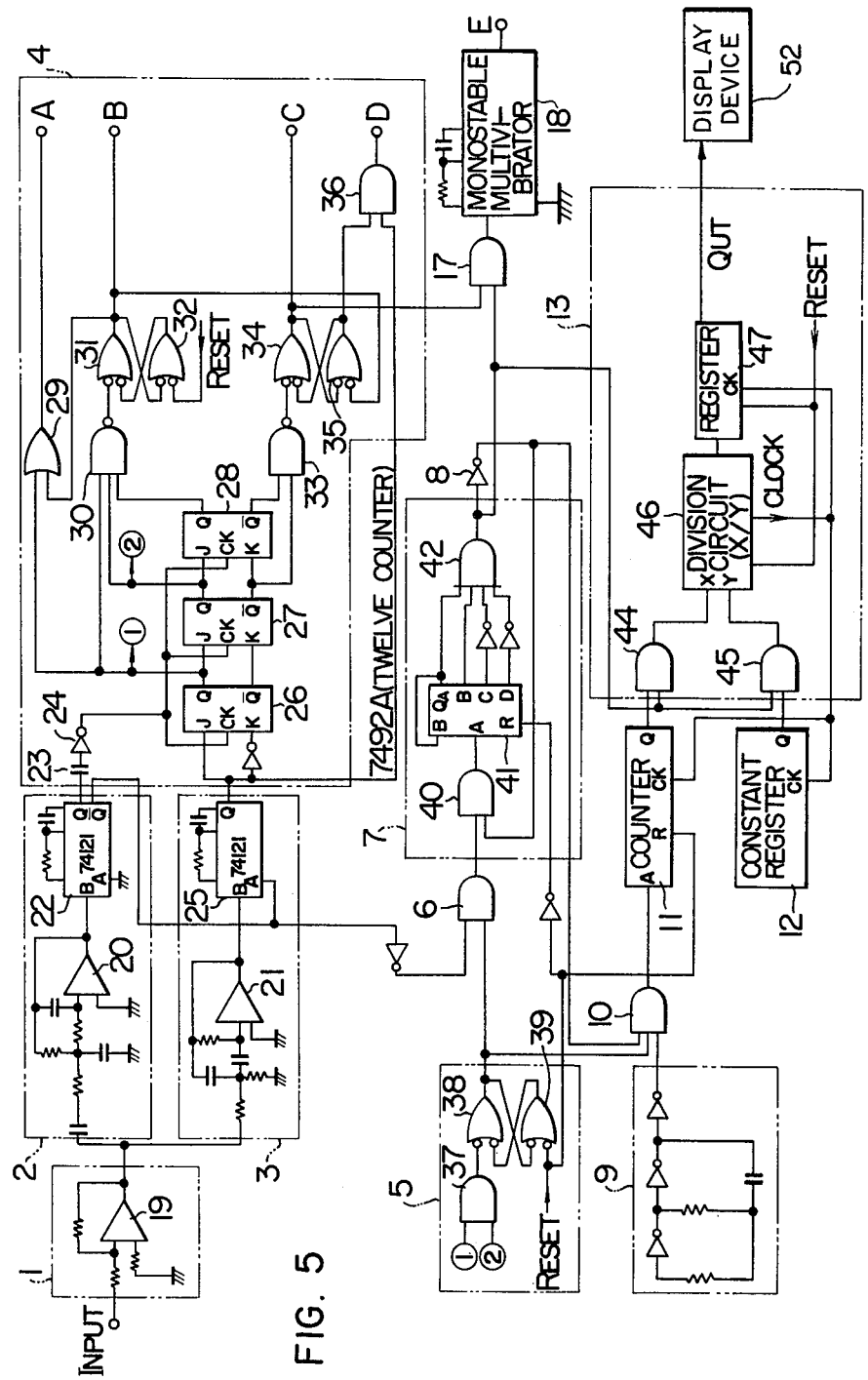
FIG. 5 is a detailed circuit arrangement of the block diagram shown in FIG. 1.

A detailed circuit of the embodiment of this invention is shown in FIG. 5. In the diagram amplifier 1 is an operational amplifier, pulse detection filter 2 is a combination of a lowpass filter 20 and a monostable multivibrator 22, and Korotkoff's sound separation filter 3 is a combination of a bandpass filter 21 and a monostable multivibrator 25. In blood pressure meter logic circuit 4, flip-flops 26, 27 and 28 constitute a shift register and outputs of the monostable multivibrator 25 are successively read. A clock signal for reading is generated by differentiating the output of the monostable multivibrator 22 by a capacitor 23 and an inverter 24. When Korotkoff's sounds are continously read three times, RS flip-flops 31 and 32 are set via an inverter 30, and an output B is set at a high level to obtain a systolic blood pressure determination signal. Since an output terminal A is set at a high level when the Korotkoff's sounds is first received, the level of blood pressure being held at that time indicates the systolic blood pressure. In order that the diastolic blood pressure can be set through means 33 when there is no consecutive Korotkoff's sounds for more than two times after the determination of the systolic blood pressure, RS flip-flops 34 and 35 are provided. After determining the diastolic blood pressure a terminal C is set at a high level. An output terminal D supplies Korotkoff's sound output, but after the determination of the diastolic blood pressure, an AND circuit 36 is inhibited and no output is produced. A pressure level at the time when a final Korotkoff's sound is delivered indicates the diastolic blood pressure. The counter 5 comprises flip-flops 26 and 27, an AND circuit 37 and RS flip-flops 38 and 39. The counter 7 consists of a 7492A counter 41 and an AND circuit 42 having four input terminals which is provided for counting ten pulses. When the counter 7 counts ten pulses and the output of the AND circuit is set at a high level the output of the AND circuit 40 is blocked via the inverter 8 to maintain the counter 7 at the high level. Numeral 11 designates a shift register having a series input and a series output, and numeral 12 is a constant register. At the end of counting of 10 pulses gates 44 and 45 are opened, the data stored in registers X and Y are successively fed to a division circuit 46 in response to a clock signal coming from the division circuit 46, and then calculated data is supplied to a register 47. The output of register 48 is displayed on the display device 52. The division circuit 46 may be constituted in various ways employing a subtraction circuit but since such a constitution is well known it is omitted here.

In this embodiment both the Korotkoff's sounds and the pulse sound signals are detected by the same single microphone. However, the pulse sound signals may also be detected by an electrocardiograph, sphygmograph and other known means.

As described above an apparatus according to this invention permits simultaneous measurement of the pulse rate together with the measurement of blood pressure by the simultaneous detection of pulse sound during the blood pressure measurement, and also enables simultaneous or selective display of the pulse rate by an automatic digital blood pressure meter. The apparatus also simultaneously detects a heart beat signal from a Korotkoff's sound detection microphone signal and thus enables simultaneous measurement of the blood pressure and the pulse rate without mounting other detectors to the body of the examinee, which enables the diagnosis of the circulatory system of human body to be conducted in a short time with more precision.

Further, even when either the determination of the diastolic blood pressure or the measurement of the pulse rate is finished prior to the completion of the other, a signal indicating the termination of the entire measurement is generated for the first time when both of the above measurements are finished, so that in the apparatus which simultaneously and automatically conducts the measurements of blood pressure and sphygmus the apparatus according to this invention eliminates erroneous operation and troublesome measurements and thus has advantages over conventional apparatus.

What is claimed is:

1. In a blood pressure measuring apparatus having a blood pressure meter logic circuit for determining a patient's systolic and diastolic blood pressures utilizing a Korotkoff's sound signal and a heart beat signal, the improvement which enables simultaneous measurement of blood pressure and pulse rate comprising:

a microphone associated with a cuff device for producing an electric signal containing a Korotkoff's sound signal and a pulse rate sound signal;

filter means connected to said microphone for separating said Korokoff's sound signal and said pulse rate sound signal;

count initiating means connected to receive said Korotkoff's sound signal and said pulse rate sound signal for producing a count initiating signal after at least two Korotkoff's sound signals have been counted successively in synchronism with said pulse rate sound signal;

counting means connected to said count initiating means for measuring a time period from reception of said count initiating signal until a predetermined number of pulse rate sound signals are counted;

division means connected to said counting means for calculating said pulse rate by dividing said predetermined number of pulse rate sound signals by said time period;

means for providing a signal indicating completion of a diastolic blood pressure measurement by said blood pressure meter logic;

means for providing a signal indicative of termination of counting of said predetermined number of pulse rate sound signals by said counting means;

means for generating a signal indicating completion of both the blood pressure measurement and the pulse rate measurement, said signal generating means generating said completion signal in response to receipt of said signal indicating completion of said diastolic blood pressure measurement and said signal indicating termination of counting; and, display means connected to said division means for displaying the calculated pulse rate.

2. A blood pressure measuring apparatus according to claim 1, wherein said filter means comprises a first filter for passing pulse rate sound signals and a second filter for passing Korotkoff's sound signals.

3. A blood pressure measuring apparatus according to claim 1, wherein said count initiating means includes a counter for producing a first level output signal after at least two successive Korotkoff's sound signals have been counted and an AND gate circuit connected to receive said first level signal and said pulse rate sound signals from said filter means for passing said pulse rate sound signals to said counting means after said first level output signal has been received.

* * * * *